United States Patent [19]
Bakalyar et al.

[11] Patent Number: 5,159,613
[45] Date of Patent: Oct. 27, 1992

[54] SIDE-BAND GENERATOR

[75] Inventors: Donovan M. Bakalyar, Dearborn, Mich.; Yong-Sung Paek, Seoul, Rep. of Korea

[73] Assignee: William Beaumont Hospital, Royal Oak, Mich.

[21] Appl. No.: 503,288

[22] Filed: Apr. 2, 1990

[51] Int. Cl.$^5$ .............................................. H03C 1/52
[52] U.S. Cl. ..................................... 375/61; 332/170; 455/109
[58] Field of Search ......................... 375/61; 332/170; 455/109

[56] References Cited

U.S. PATENT DOCUMENTS

| | | | |
|---|---|---|---|
| 3,317,840 | 5/1967 | Guttman et al. | 375/61 |
| 3,501,594 | 3/1970 | Thrasher et al. | 455/47 |
| 3,605,017 | 9/1971 | Chertok et al. | 375/61 |
| 3,611,144 | 10/1971 | Harmon, Jr. | 375/43 |
| 3,806,655 | 4/1974 | Hekimian et al. | 455/47 |
| 3,955,143 | 5/1976 | Collins | 375/61 |
| 4,050,024 | 9/1977 | Winston, IV | 455/203 |
| 4,310,920 | 1/1982 | Hayes | 455/109 |

OTHER PUBLICATIONS

Articles: Signetics, "1987 Linear Data Manual vol. I: Communications" pp. 4-79-4-86.
"Communication Systems", 2nd Ed., Simon Haykin, Published by John Wiley & Sons, pp. 137-149.
"Communication Systems, An Introduction to Signals and Noise in Electrical Communication", 3rd Ed., A. Bruce Carlson, Published by McGraw-Hill Book Co. pp. 213-218.

Primary Examiner—Stephen Chin
Assistant Examiner—Young Tse
Attorney, Agent, or Firm—Harness, Dickey & Pierce

[57] ABSTRACT

An upper and lower side-band generator comprised of a combination of combinational logic circuits. In a preferred embodiment the invention utilizes a substantially square wave sync output associated with carrier and modulator signal generators. A lower side-band signal is generated by synchronizing the transitions of a modulator signal with the transitions of a carrier signal, mixing the synchronized signal with the carrier signal, and filtering the resulting mixed signal. An upper side band signal is generated by synchronizing the carrier and modulator signals, delaying the resulting synchronized signal, and mixing the delayed, synchronized signal and the carrier signal.

17 Claims, 6 Drawing Sheets

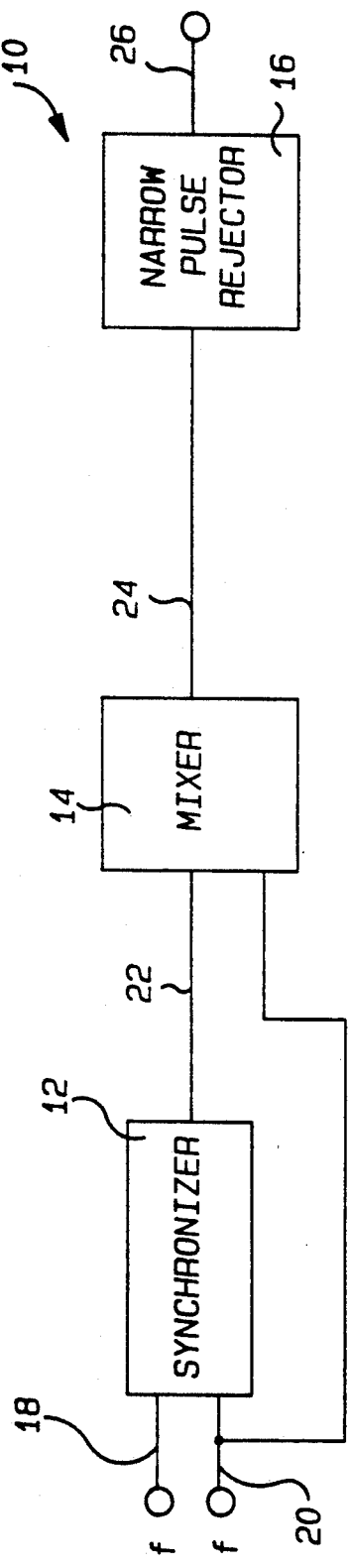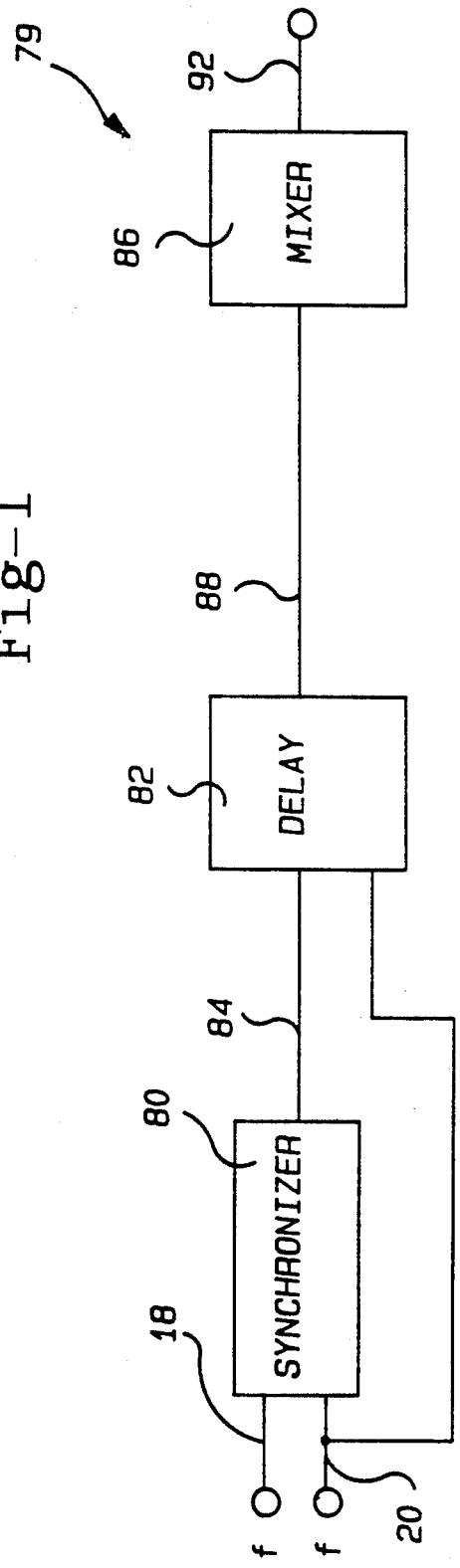

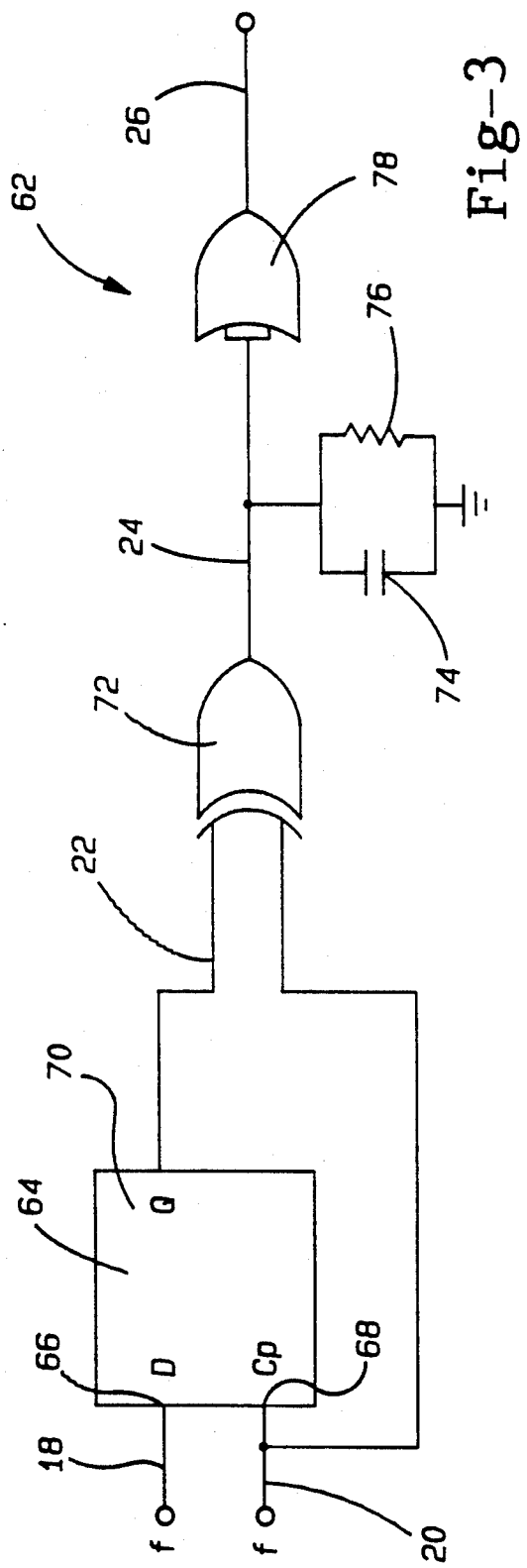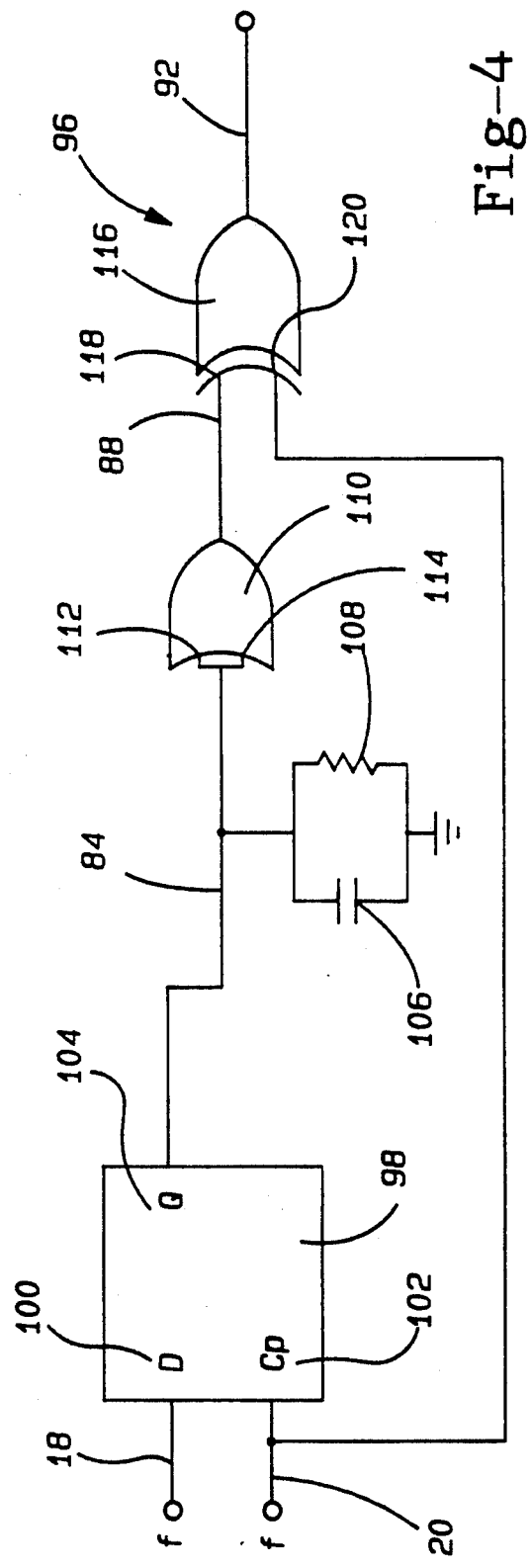

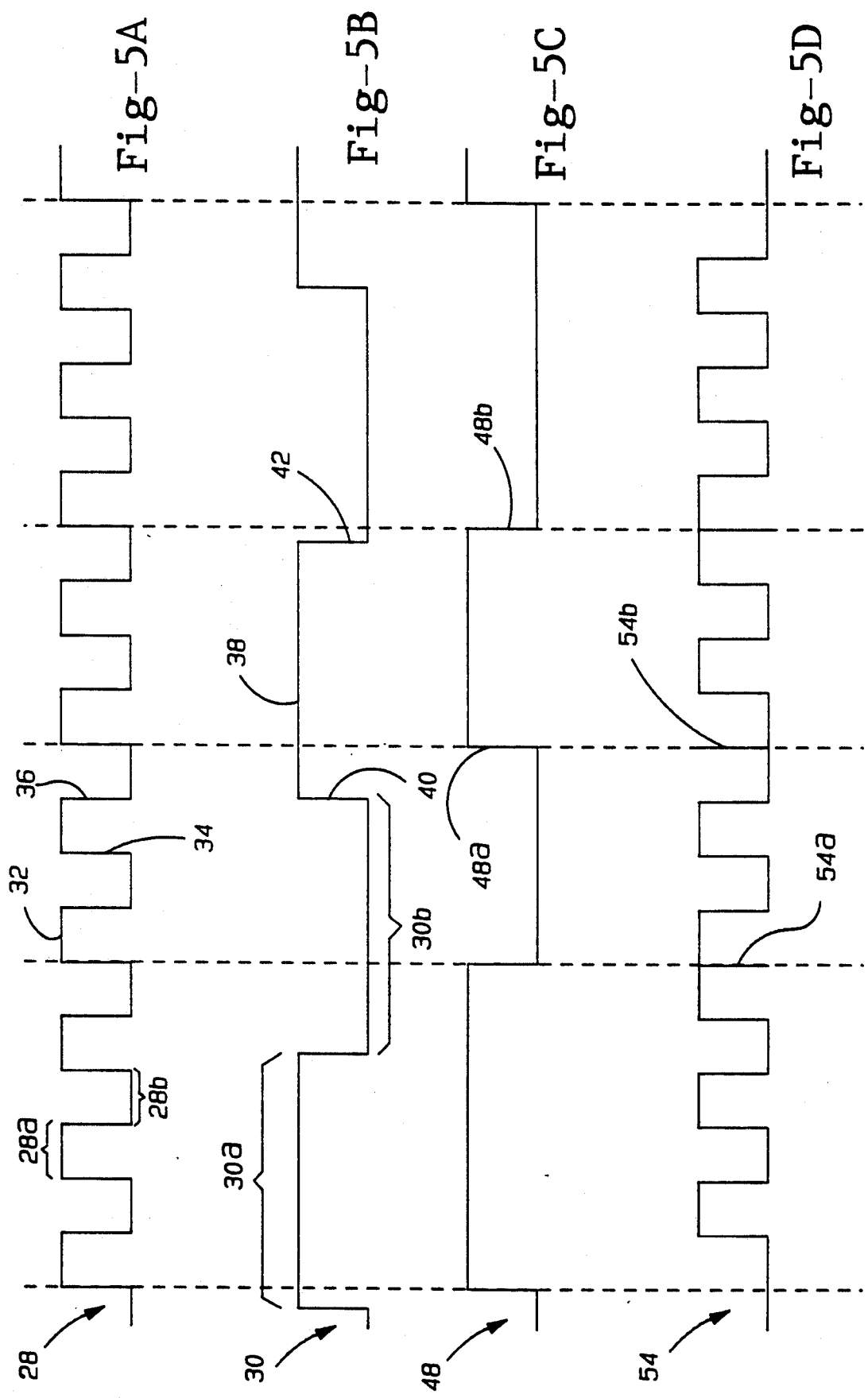

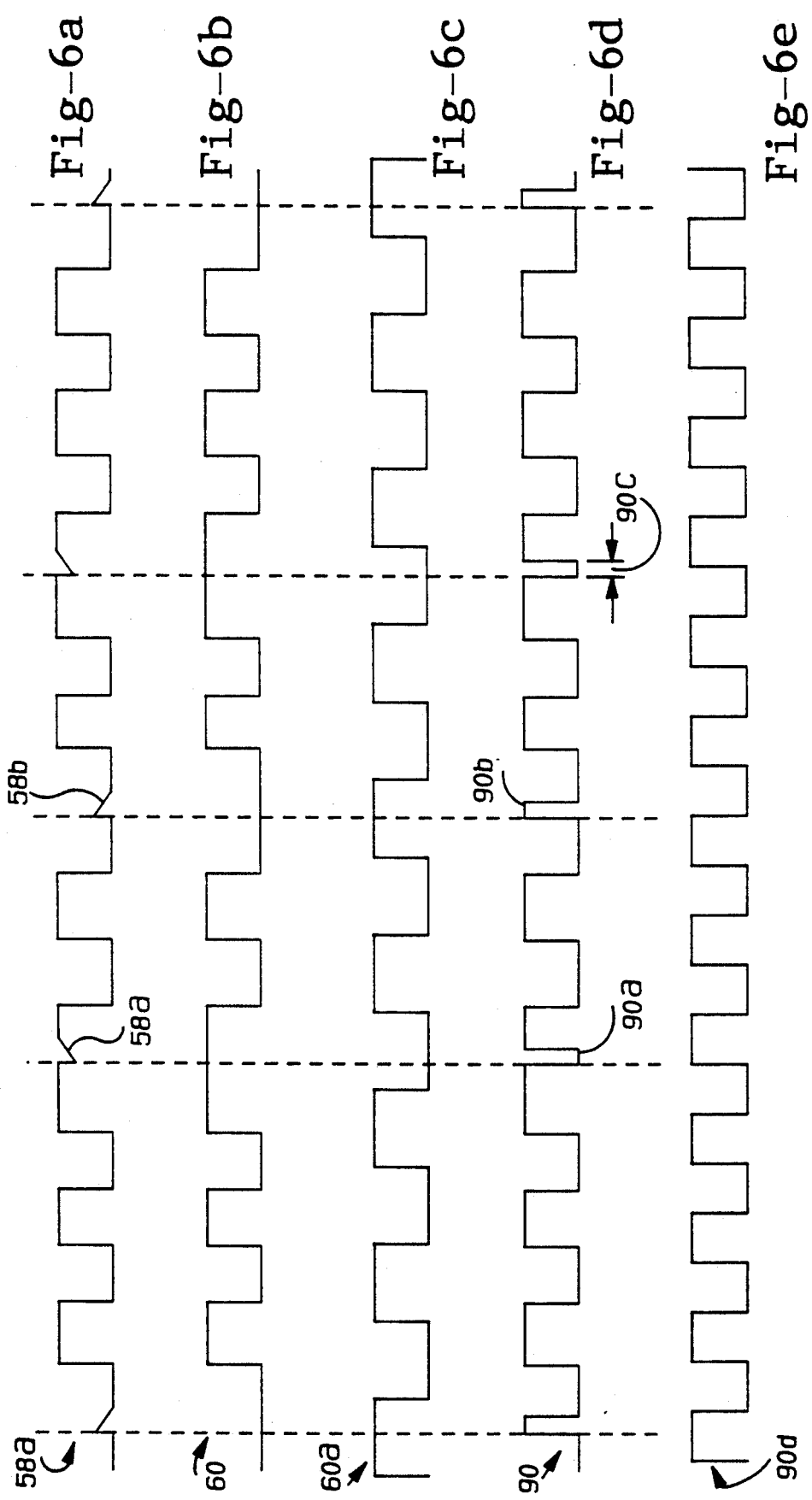

SIDE-BAND GENERATOR

BACKGROUND OF THE INVENTION

1. Technical Field

This invention relates to a side-band generator, and more particularly to a side-band generator which may be used in tissue characterization applications and which generates upper and lower side-band signals.

2. Discussion

Side-band generators are generally used in a plurality of electrical communication applications. One use of these side-band generators is associated with the detection of acoustical signals generated in a non-linear media, such as tissues. In this application, a high frequency sinusoidal ultrasound wave (i.e., a carrier) is typically transmitted, along with a low frequency sinusoidal wave (i.e., a modulator), into a sample of tissue which is desired to be studied relative to the health associated therewith. The high frequency and low frequency signals then acoustically interact within the tissue and the resultant mixing of the signals, when detected by an ultrasonic transducer, produces a characteristic electrical signature signal which is then used to properly characterize the tissue sample.

This electrical signature signal contains both an upper side-band component (having a frequency associated therewith being equal to the sum of the frequencies of the carrier and modulator signals) and a lower side-band component (having a frequency associated therewith, being equal to the difference of the frequencies of the carrier and modulator signals). In order to properly generate this signature, the upper or lower side-band signals must first be separated from the resultant electrical signal. A current methodology associated with this electrical signal characterization incorporates the use of a lock-in amplifier. While this lock-in amplifier is useful in the characterization of the electrical signature signal, it requiers the generation of the side-band frequency of interest (upper or lower) as a reference input thereto. It is useful that this side-band be generated from the auxiliary ("sync") output apertures of the carrier and modulator generators. The waveforms from these "sync" outputs are typically square waves of fixed amplitude.

Techniques which currently are used to generate side-band frequencies from the "sync" output apertures are relatively inefficient and require relatively complex electronic apparatus. These techniques may require the use of sharp cut-off filters, local oscillators, balanced mixers, synthesis of sinusoidal waves from the square waves, multiple phase-locked loops, phase shift circuits, or the generation of signals with exactly four times the frequency of the carrier of modulator waves. These complexities can make the circuitry susceptible to faults and can either severely limit the frequency range of operation of the circuitry or require the inclusion of active tuning circuitry.

SUMMARY OF THE INVENTION

According to the teachings of the preferred embodiment of this invention, an upper and lower side-band signal is generated by the use of a combination of combinational logic circuit entities. The side-band generating apparatus of this invention utilizes the substantially square wave "sync" output associated with the carrier and modulator signal generators and then, for the generation of the lower side-band signal, synchronizes the transitions of the modulator signal with the transitions of the carrier signal, mixes the synchronized signal with the carrier signal, and filters the resulting mixed signal, thus producing the desired lower side-band signal.

For the generation of the upper side-band signal, the carrier and modulator signals are synchronized, the synchronized signal is delayed, and the delayed signal and the carrier signal are mixed, thereby producing the upper side-band signal.

These and other aspects, features, and advantages of this invention will be more readily understood by reviewing carefully the following detailed description taken in conjunction with the accompanying drawings and claims.

BRIEF DESCRIPTION OF DRAWINGS

For a more complete understanding of the present invention relative to the advantages thereof, reference may be made to the following detailed description taken in conjunction with the accompanying drawings in which:

FIG. 1 is a block diagram of the lower side-band generator of the preferred embodiment of this invention;

FIG. 2 is a block diagram of the upper side-band generator of the preferred embodiment of this invention;

FIG. 3 is an electrical schematic diagram associated with the lower side-band generator generally shown in FIG. 1;

FIG. 4 is an electrical schematic diagram associated with the upper side-band generator generally shown in FIG. 2;

FIG. 5A is a diagram of a typical carrier signal generated by the present invention;

FIG. 5B is a diagram of a typical modulator waveform generated by the present invention;

FIG. 5C is a diagram of a typical output waveform generated by the synchronizer of the present invention;

FIG. 5D is a diagram of a typical output waveform generated by the mixer of the present invention;

FIG. 6A is a diagram of the output waveform of FIG. 5D after the aberrations in the waveform of FIG. 5D have been broaded by the parallel resistor-capacitor combination of FIG. 3;

FIG. 6B is a diagram of the output waveform generated by the narrow pulse rejector of FIG. 1;

FIG. 6C is a diagram of the output waveform of FIG. 6B after the waveform has been passed through a typical phase lock loop circuit;

FIG. 6D is a diagram of the output waveform generated by the mixer of FIG. 2;

FIG. 6E is a diagram of the waveform of FIG. 6D after the waveform has been refined by a typical phase lock loop circuit.

DESCRIPTION OF THE PREFERRED EMBODIMENT

Figure 2A:
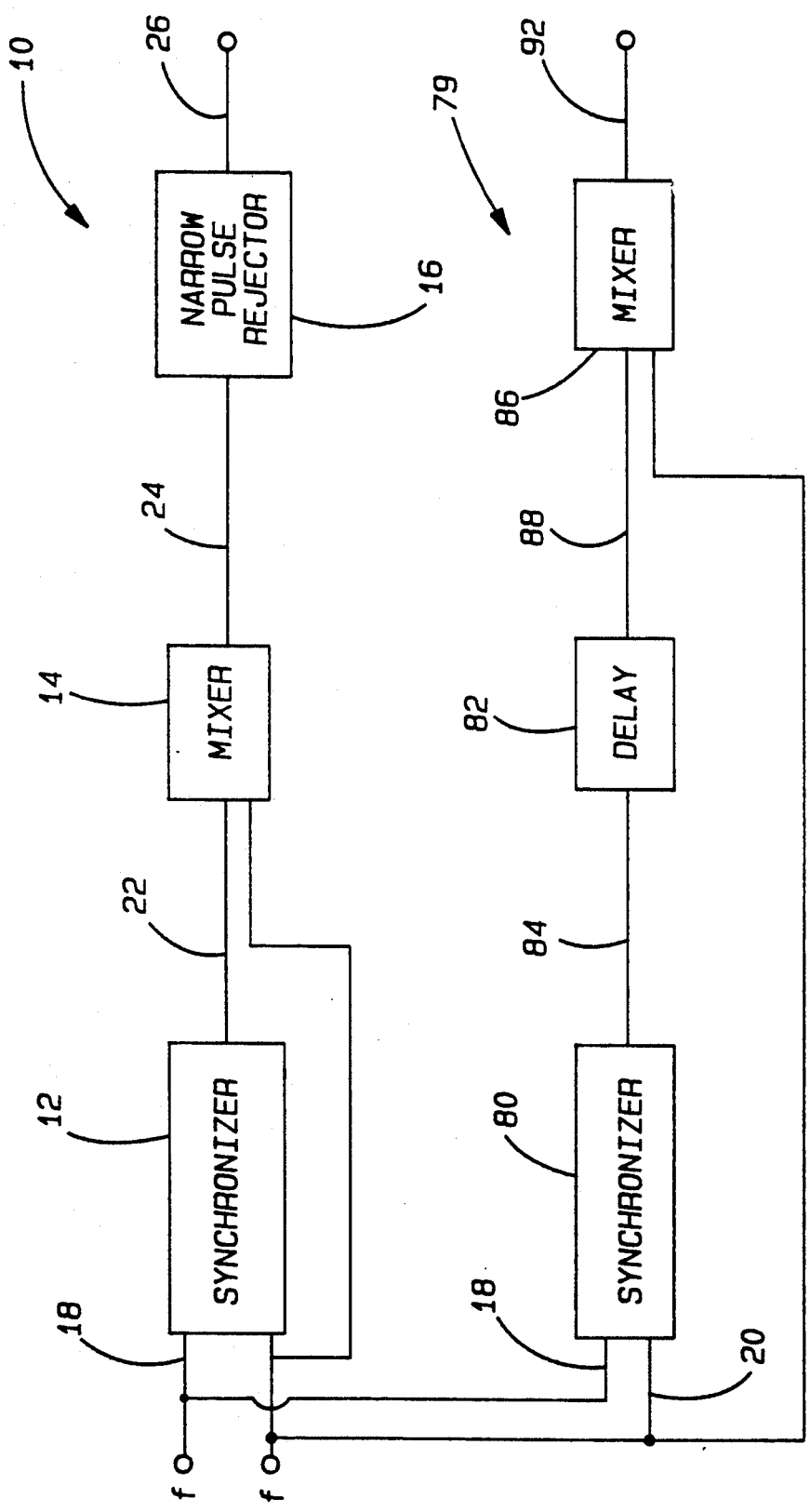
FIG. 2A is a block diagram of an upper and lower side band generator in accordance with preferred embodiments of the invention.

Referring now to FIG. 1, there is shown a lower side-band generator 10 made in accordance with the teachings of the preferred embodiment of this invention and including a synchronizer 12, a mixer 14, and a narrow pulse rejector 16. Specifically, synchronizer 12 has its inputs coupled to a typical modulator signal on bus 18 and to a typical carrier signal on bus 20. Modulator signals on busses 18 and 20 are typically of a rectangular pulse train nature. Synchronizer 12 further has an output coupled to an input of mixer 14 by bus 22 and mixer 14 has an additional input associated therewith coupled to bus 20. The output of mixer 14 is placed onto bus 24 and is input into narrow pulse rejector 16 which produces an output on bus 26.

In operation, synchronizer 12 synchronizes the transitions of the modulator signal on bus 18 to the transitions of the carrier signal on bus 20. This is best shown in FIGS. 5A and 5B where the typical carrier signal on bus 20 is illustrated by signal 28 and the typical modulator signal on bus 18 is illustrated by signal 30. Specifically, signal 28 contains a plurality of pulses 32, each having a leading upwardly transitioning edge 34 and a trailing downwardly transitioning edge 36 associated therewith. The typical modulator signal 30 of FIG. 5B contains a plurality of pulses 38, having a leading upwardly transitioning edge 40 and a trailing downwardly transitioning edge 42 defining a width 30a being substantially greater than the width 28a associated with the plurality of pulses 32 defined by signal 28 of FIG. 5A. For convenience, the duty cycles of the waveforms 28 and 30 are shown in FIGS. 5A and 5B as being about 50% each, although it should be appreciated that the duty cycles could vary considerably from 50%. In addition, it will be convenient for the purpose of discussion to denote the time periods between transitioning edges on waveforms 28 and 30 as the "half-cycle times", as indicated at 28a and 28b in FIG. 5A and 30a and 30b in FIG. 5B.

With reference now to FIG. 5C, synchronizer 12 (FIG. 1) produces an output signal 48 onto bus 22. Signal 48 is substantially similar to signal 30, except that an upward or downward edge (48a and 48b respectively) associated with signal 48 may not occur until a leading edge 34 of a pulse 32 is occurring. Alternatively, synchronization to the trailing edges 36 of the pulses in signal 28 could be employed.

Mixer 14 receives signal 48, as an input thereto by bus 22, and also receives signal 28 through bus 20. Mixer 14 produces output signal 54, shown in FIG. 5D, which is logically low if and only if both signals 28 and 48 represent the same logical value (i.e., either both being logically low or both being logically high at substantially the same instant of time). Mixer 14 will perform equally as well if it has the opposite logic, i.e., if output signal 54 is logically high if and only if both signals 28 and 48 represent the same logical value. Additionally, signal 54 is seen to typically contain a plurality of narrow negative pulses 54a and narrow positive pulses 54b, resulting from the typical mismatch, in time, between the transitions in the output of the synchronizer 12 on bus 22 and the signal 28 associated with bus 20.

Signal 54 is then placed onto bus 24 by mixer 14 and input into the narrow pulse rejector 16. The narrow pulse rejector ignores any negative 54a or positive pulses 54b which are of insufficient duration (as determined by the properties of the narrow pulse rejector 16 thereto) and produces a signal 60, shown in FIG. 6B, which substantially represents the lower side-band signal associated with signals 18 and 20. In signal 60, the transition is delayed one carrier half-cycle time for every transition in the modulator insuring, for a given period of time, that the number of transitions in signal 60 is equal to the number of transitions in signal 28 less the number of transitions in signal 48. Thus the average frequency of signal 60 is precisely the lower side-band frequency. Signal 60 may be further refined by being passed through a typical phase lock loop circuit and this refined signal (i.e., substantially jitter free) is shown as signal 60a in FIG. 6C.

Turning now to FIG. 3, there is shown circuit 62 comprising an embodiment of the lower side-band generator 10 (whose block diagram is shown generally in FIG. 1). Specifically, synchronizer 12 may be represented by a typical D- flip-flop 64, having its "D" input port 66 coupled to bus 18 and its "clock" input port 68 is coupled bus 20. The "Q" output port 70 of flip-flop 64 is coupled to bus 22 and produces signal 48 therefrom. Further, mixer 14 may be represented by a typical Exclusive-OR gate 72 having inputs coupled to buses 20 and 22 and having its output coupled to bus 24. Exclusive-OR gate 72 produces signal 54 onto bus 24.

Lastly, the narrow pulse rejector may be represented by the parallel arrangement of capacitor 74 and resistor 76 along with the OR-gate 78. A Schmidt Trigger, however, could be used instead of the OR-gate if so desired. Capacitor 74 and resistor 76 have one common end thereof coupled to electrical ground and an opposite end coupled to bus 24. OR-gate 78 has its input coupled to bus 24. Operationally, capacitor 74 and resistor 76 act to integrate the sharp narrow transitions 54a and 54b of signal 54, thereby producing broad aberrations 58a and 58b of considerably reduced amplitude of signal 58. These reduced amplitude signals are rejected by the discrimination properties of gate 78 which outputs signal 60 therefrom, defining the lower side-band signal.

Turning now to FIG. 2, there is shown a block diagram of an upper side-band generator 79 of the preferred embodiment of this invention, and containing a synchronizer 80 (being substantially similar to synchronizer 12), having inputs coupled to buses 18 and 20 and further having an output coupled to delay circuit 82 via bus 84. The output of delay circuit 82 is placed upon bus 84 and is input to mixer 86 (which is substantially similar to mixer 14) via bus 88. Mixer 86 is further coupled, at an input thereof, to bus 20.

A combined upper and lower side band generator in accordance with FIGS. 1 and 2 is shown in FIG. 2A.

In operation, signals 28 and 30 (FIGS. 5A and 5B) are input to synchronizer 80 by buses 20 and 18 respectively and synchronizer 80 produces signal 48 (FIG. 5C) on bus 84 to delay circuit 82. Delay circuit 82 then delays signal 48 and places this delayed signal onto bus 88 to mixer 86. Mixer 86 then produces output signal 90 (FIG. 6D) onto bus 92, which is the upper side-band signal associated with signals 28 and 30.

Output signal 90, as shown in FIG. 6D, is substantially similar to signal 54, except that the narrow pulses 54a and 54b in FIG. 5D are deliberately expanded to widths 90a and 90b and are integrally formed within signal 90. This width expansion of pulses 54a and 54b is due to the delay associated with delay circuit 82. That is, signal 48 (FIG. 5C) is prevented from reaching mixer 86 until a delay, associated with circuit 82, has passed resulting in aberrations 90a and 90b having widths 90c associated therewith.

Referring now to FIG. 4, there is shown an electrical circuit 96, which is representative of the upper sideband generator 79 of FIG. 2. Specifically, synchronizer 80 may be represented by a typical "D" flip-flop 98, having its "D" port 100 coupled to bus 18 and having its "clock" port 102 coupled to bus 20. Further, flip-flop 100 has its "Q" port 104 coupled to bus 84, which produces signal 48 (FIG. 5C) therefrom.

Delay circuit 82 is represented, in the circuit embodiment of FIG. 4, by resistor 108, capacitor 106 and OR-gate 110. The parallel arrangement of capacitor 106 and resistor 108, coupled at one common end thereof to bus 84 and at their opposite common end to electrical ground, serve to lengthen the transitioning time of the Q port 104. Thus the length of time required to change voltage on bus 84 from its lower value to its upper value or the length of time required to change output voltage on bus 84 from its upper value to its lower value can no longer be considered as substantially instantaneous but rather as a finite length of time determined by the values of capacitor 106 and resistor 108 thereof. The discriminating properties of OR-gate 110 (or, substantially as before with the lower side-band circuit, a Schmidt Trigger circuit instead of the OR-gate) then produce delayed transitions so as to substantially reproduce signal 48 onto bus 88 at a later instant of time from the time that signal 48 first appeared on inputs 112 and 114.

Further, as shown in FIG. 4, mixer 86 may be represented by an Exclusive-OR gate 116, having one input 118 coupled to bus 88 and another input 120 coupled to bus 20. Gate 116 then produces signal 90 on bus 92, which is defined to be a logical one at all times, except when delayed signals 48 and signal 28 are substantially similar.

The signal 90 of FIG. 6D substantially represents the upper side-band signal associated with signals 18 and 20. Signal 90 is substantially like signal 54 except that the narrow pulses 54a and 54b have been widened sufficiently in time to 90a and 90b to ensure that the mixer 86 will recognize the transitions as true level changes.

For signal 90, a pulse is added to lower side-band signal 60 for every transition in the modulator insuring, for a given period of time, that the number of transitions in signal 90 is equal to the number of transitions in signal 60 plus twice the number of transitions in signal 48. Thus the average frequency of signal 90 is precisely the upper side-band frequency. Signal 90 may be further refined by being passed through a typical phase lock loop circuit and this refined signal (i.e., substantially jitter free) is shown as signal 90c (FIG. 6E).

Figure 7:
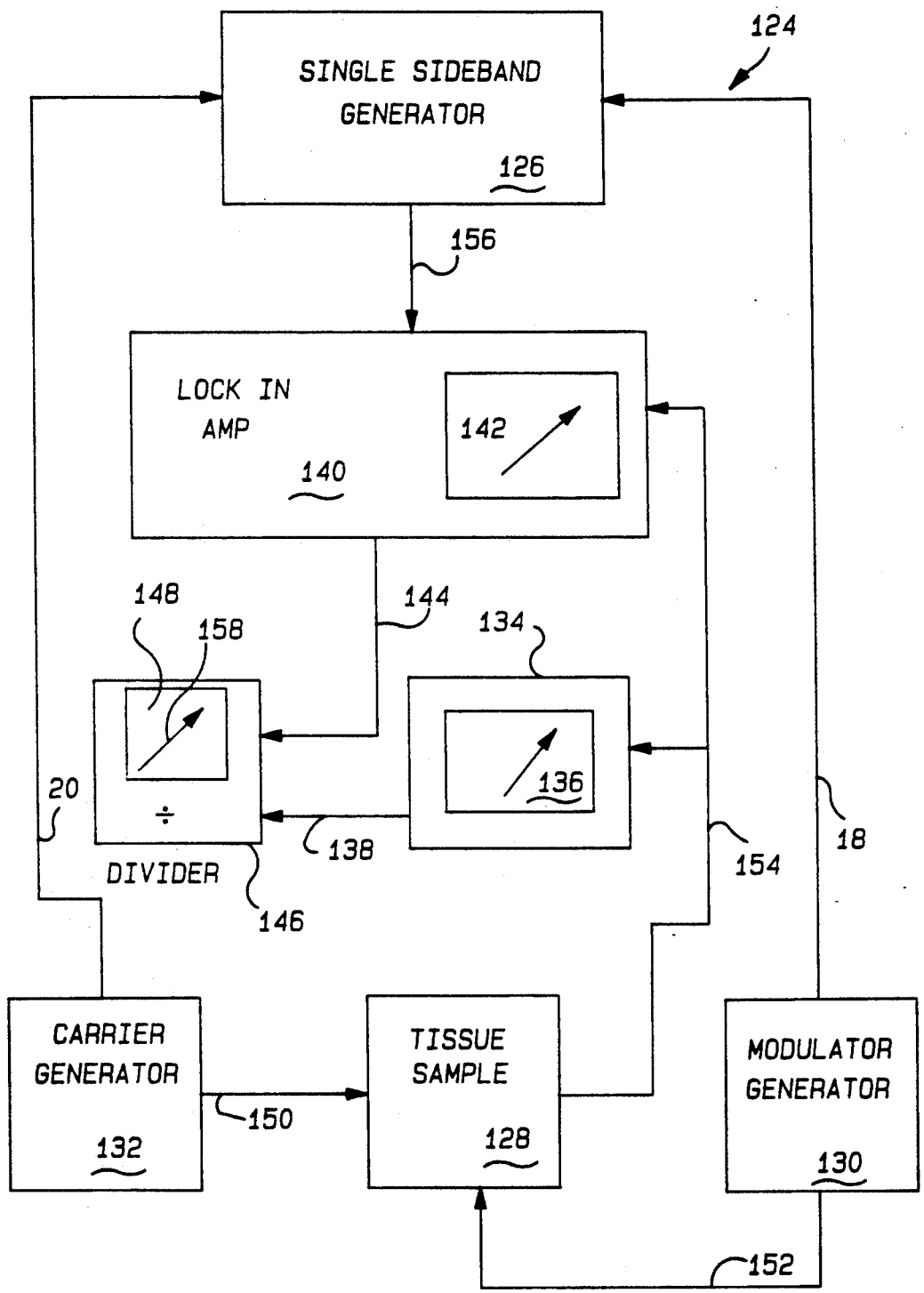
FIG. 7 is a illustration of the use of the side-band generator generally shown in FIGS. 1 and 2, as used within a typical tissue characterization system.

Referring now to FIG. 7, there is shown a tissue characterization system 124, employing a single side-band (SSB) generator 126, consisting of either the lower side-band (LSB) generator 10 or the upper side-band (USB) generator 79 of the preferred embodiment of this invention. System 124 is used to characterize or determine the health of a tissue sample 128 and further contains a typical modulator signal generator 130, a typical carrier signal generator 132, a typical AC voltmeter 134 having a typical voltage meter 136 and a typical output bus 138 thereon, a typical "lock-in" amplifier 140 having a typical voltage meter 142 and a typical output bus 144 thereon, and a typical divider circuit 146 having a typical voltage meter 148 thereon. Carrier signal generator 132 typically transmits a sinusoidal signal on bus 150 and a square wave "sync" signal of fixed amplitude on bus 20 which is identical in frequency to the signal on bus 150. Modulator signal generator 130 typically transmits a sinusoidal signal on bus 152 and a square wave "sync" signal of fixed amplitude on bus 18 which is identical in frequency to the signal on bus 152.

In operation, generators 132 (carrier) and 130 (modulator) drive bus lines 150 and 152 with sinusoidal signals which, in turn drive ultrasonic transducers, producing ultrasonic waves which are then input into tissue sample 128 where they mix and non-linearly interact therein producing side-bands. The carrier and side-bands are detected by a third ultrasonic transducer and the resultant signal is placed on bus 154 which proceeds therefrom to amplifiers 134 and 140. AC voltmeter 134 detects the entire signal, the fraction which are side-bands thereof being negligible. Amplifier 140 then detects a single side-band only by the use of the SSB signal on bus 156 which is produced by generator 126 as previously discussed. (Bus 154 is the same as bus 26 for the LSB generator 10 or bus 92 for the USB generator 79). Amplifier 140 then generates a signal on bus 144 which is divided by the signal on bus 138 using the circuitry of divider 146 therein. The quotient is displayed on divider 146 which may then be used to visually enable a user of system 124 to determine the state of tissue sample 126 by direct observance of the position of indicator needle 158 therein. The use of generator 126 within system 124, allows for greater overall simplicity of system 124 and for more reliable performance by meter 148 and hence, greater accuracy in the characterization of the tissure sample 128.

It is to be understood that the invention is not to be limited to the exact construction or method illustrated. In particular, it should be understood that the logic circuits employed are not restricted to electronic circuits but may utilize in whole or in part any other means (i.e., optical or magnetic) to achieve the same logical tasks. Accordingly, various changes and modifications may be made without departing from the spirit and scope of the invention, as described in the subjoined claims that follows.

What is claimed is:

1. A lower side-band generator comprising:
   synchronization means having a plurality of inputs and an output, said inputs being coupled to a carrier and to a modulator signal, said carrier and said modulator signals having upward and downward transitions associated therewith, for modifying said modulator signal by causing said upward and said downward transitions of said modulator signal to occur only upon one of said transitions of said carrier signal, and for outputting said modified modulator signal therefrom, and
   mixer means having a plurality of inputs and an output, one of said inputs being coupled to said output of said synchronization means and the other said input being coupled to said carrier signal, for modifying said carrier signal by delaying said upward and said downward transitions of said carrier signal according to said modified modulator signal and for creating a lower side-band signal from said modified carrier signal.

2. The lower side-band generator of claim 1, wherein said modified carrier signal has a plurality of pulses of short duration associated therewith, said lower side-band generator further comprising narrow pulse rejector means coupled to said output of said mixer means, for eliminating said pulses of short duration from said modified carrier signal.

3. The lower side-band generator of claim 1, wherein said transitions of said carrier signal comprise upward transitions.

4. The lower side-band generator of claim 1, wherein said transitions of said carrier signal comprise downward transitions.

5. The lower side-band generator of claim 1, wherein said synchronization means comprises a "D" flip-flop.

6. The lower side-band generator of claim 1, wherein said mixer means comprises an Exclusive-OR gate.

7. The lower side-band generator of claim 1, wherein said mixer means comprises an Exclusive-OR gate.

8. An upper side-band generator comprising:
synchronization means having a plurality of inputs and an output, one of said inputs being coupled to a carrier signal and the other said input being coupled to a modulator signal, said carrier and said modulator signals having upward and downward transitions associated therewith, for modifying said modulator signal by causing said upward and said downward transition of said modulator signal to occur only upon one of said transitions of said carrier signal, and for outputting said modified modulator signal therefrom;
delay means having an input and an output, said input being coupled to said output of said synchronization means, for delaying said modified modulator signal and for outputting said delayed signal from said output of said delay means; and
mixer means having a plurality of inputs and an output, one of said inputs being coupled to said delay means and the other said input being coupled to said carrier signal, for modifying said carrier signal by delaying said upward and said downward transitions of said carrier signal according to said signal output from said delay means and for creating an upper side-band signal from said modified carrier signal.

9. The upper side-band generator of claim 8, wherein said transitions of said carrier signal comprise upward transitions.

10. The upper side-band generator of claim 8, wherein said transitions of said carrier signal comprise downward transitions.

11. The upper side-band generator of claim 8, wherein said synchronization means comprises a "D" flip-flop.

12. The upper side-band generator of claim 8, wherein said mixer means comprises an Exclusive-OR gate.

13. An upper and lower side-band generator comprising:
synchronization means having a plurality of inputs and an output, one of said inputs being coupled to a carrier signal and the other said input being coupled to a modulator signal, said carrier and said modulator signals having upward and downward transitions associated therewith, for modifying said modulator signal by causing said upward and said downward transitions of said modulator signal to occur only upon one of said transitions of said carrier signal and for outputting said modified modulator signal from said output thereof;
first mixer means having a plurality of inputs and an output, one of said inputs being coupled to said synchronization means and the other said input being coupled to said carrier signal, for modifying said carrier signal by delaying said upward and said downward transitions of said carrier signal according to said modified modulator signal and for creating a lower side-band signal from said modified carrier signal;
delay means having an input and an output, said input being coupled to said synchronization means for delaying said modified modulator signal and for outputting said delayed signal therefrom; and
second mixer means having a plurality of inputs and an output, one of said inputs being coupled to said output of said delay means and the other said input being coupled to said carrier signal, for modifying said carrier signal by delaying said upward and said downward transitions of said carrier signal according to said signal output from said delay means and for creating an upper side-band signal from said modified carrier signal.

14. The upper and lower side-band generator of claim 13, wherein said delayed carrier signal has a plurality of pulses of short duration associated therewith, said lower side-band generator further comprising filter means coupled to said output of said first mixer means for eliminating said pulses of short duration from said delayed carrier signal.

15. The upper and lower side-band generator of claim 13, wherein said transitions of said carrier signal comprise upward transitions.

16. The upper and lower side-band generator of claim 13, wherein said transitions of said carrier signal comprise downward transitions.

17. The upper and lower side-band generator of claim 13, wherein said second mixer means comprises an Exclusive-OR gate.

* * * * *